(12) United States Patent
Kirollos et al.

(10) Patent No.: US 9,110,028 B2
(45) Date of Patent: Aug. 18, 2015

(54) SORBENT MEDIA EXHAUSTION INDICATOR

(71) Applicants: Kirollos Salama Kirollos, Virginia Beach, VA (US); Michael Kirollos Kirollos, Virginia Beach, VA (US)

(72) Inventors: Kirollos Salama Kirollos, Virginia Beach, VA (US); Michael Kirollos Kirollos, Virginia Beach, VA (US)

( * ) Notice: Subject to any disclaimer, the term of this patent is extended or adjusted under 35 U.S.C. 154(b) by 195 days.

(21) Appl. No.: 13/745,024

(22) Filed: Jan. 18, 2013

(65) Prior Publication Data

US 2014/0205505 A1    Jul. 24, 2014

(51) Int. Cl.
*G01N 21/78* (2006.01)
*G01N 31/22* (2006.01)
*G01N 21/77* (2006.01)

(52) U.S. Cl.
CPC ............... *G01N 21/78* (2013.01); *G01N 31/22* (2013.01); *G01N 31/224* (2013.01); *G01N 2021/7773* (2013.01)

(58) Field of Classification Search
CPC ...... G01N 31/224; G01N 31/22; G01N 21/77; G01N 21/78; G01N 2021/7773
See application file for complete search history.

(56) References Cited

U.S. PATENT DOCUMENTS

2012/0062892 A1*  3/2012  Wendland et al. ............ 356/405
2012/0062893 A1*  3/2012  Rakow et al. ................. 356/405

\* cited by examiner

*Primary Examiner* — Jill Warden
*Assistant Examiner* — Timothy G Kingan

(57) ABSTRACT

A Sorbent media exhaustion indicator produces color change when the sorbent media is saturated. The indicator's fluid inlet attach to the fluid outlet of a sorbent media device such as filter. It includes is a hollow tube or a hollow polyhedron prism that fluids flow freely through it. The indicator also includes colorimetric sensor that changes color when exposed to trace amount of toxic fluids and a trap member that prevent toxic fluids exist in the surrounding environment from changing the color of the colorimetric sensor, hence preventing false indication of sorbent media exhaustion. Another function of the trap member is to trap toxic fluids from exiting to the surrounding environment when toxic fluids breakthrough the sorbent media device.

16 Claims, 8 Drawing Sheets

SORBENT MEDIA EXHAUSTION INDICATOR

CROSS-REFERENCE TO RELATED APPLICATION

The present invention relates to U.S. Provisional Patent Ser. No. 61/589,52 filed on Jan. 23, 2012 and claims priority therefrom.

STATEMENT REGARDING FEDERAL SPONSORED RESEARCH OR DEVELOPMENT

The subject matter of this application did not receive federal research and development funding.

FIELD OF THE INVENTION

The present invention relates generally to a direct reading system, method and apparatus for protecting against exposure to harmful environments. In this regards, the present invention relates generally to the indication of the exhaustion and saturation of sorbent media by changing color. The sorbent media exhaustion indicator (SMEI) of the present invention functions to warn the user when the sorbent media is saturated and exhausted. More particularly, the present invention relates to such a system and apparatus for the detection and indication of exhaustion and saturation of sorbent media devices such as low-flow filters, high-flow filters, carbon absorbers, carbon beds and the like (hereinafter referred to collectively as "sorbent media devices").

BACKGROUND OF THE INVENTION

SMEIs are commercially available and are used to indicate the exhaustion of carbon beds and carbon absorbers. Conventional SMEIs, commonly known as sample stream breakthrough detectors, saturation indicators or breakthrough indicators are basically constructed from a hollow clear plastic cylinder, sometimes perforated on the sides, filled with granular colorimetric indicator, capped and diffusion-vented at both ends. In operation, these devices are connected to the outlet of sorbent media devices and changes color when the sorbent media is exhausted.

A major functional drawback of the known art is the false indication of the exhaustion of the sorbent media. This occurs because the colorimetric indicator is directly exposed to the outside environment; therefore any fluid contaminant that exists in the surrounding ambient atmosphere would change the color of the indicator before the exhaustion of the sorbent media, hence producing false positive result. High humidity causes the same problem.

Another major drawback of the current devices is the deterioration of the colorimetric indicator due to light exposure. This problem also produces a false positive indication of the exhaustion of the sorbent media because the light deterioration causes color change similar to the color change due to exposure to fluid contaminants. To overcome this problem, some manufacturers cover the device with a metal or opaque plastic lid. This solution solves the problem of the deterioration of the colorimetric indicator. However, in operation, the user should frequently lift the protective lid to see whether or not there is a color change in the indicator. This is causes significant distraction to the user, especially in a workplace environment.

Another functional problem associated with the current SMEIs is their low sensitivity to targeted fluid contaminants. The hollow clear cylinder is filled with the granular colorimetric indicator in an effort to slow down the deterioration of the indicator due to light and humidity. However, the high capacity of the indicator requires larger quantities of the targeted contaminant to cause noticeable color change, hence causing a false negative result.

Accordingly, a need has risen for an SMEI with no false positive or false negative indication of the exhaustion of the sorbent media that is highly sensitive to toxic contaminant fluids and that operates independently of the surrounding environment, whether it is toxic contaminant fluids in the ambient atmosphere or the light condition.

A search of the prior art did not disclose any patents that read directly on the claims of the present invention; however, the following references were considered related.

Philip; (U.S. Pat. No. 2,951,156) reported that the residual life of carbon adsorption beds can be determined by passing beta-radiation through the adsorption bed.

Thomas; (U.S. Pat. No. 7,744,684) claims high capacity gas filter system, having a visible indicator showing when the filter is spent.

Arno, Michael J.; (U.S. Pat. No. 7,285,156) claims a dryness indicators designed to visually indicate the moisture content of compressed gas or air delivered to a point of use.

There are also numerous literature and patents on end of service life indicators (ESLI) for respiratory cartridges. These devices, generally, comprises a sensor (colorimetric or electronic) imbedded inside the respiratory cartridge and function to alert the user before the consumption of the sorbent media inside the respiratory cartridge.

The following patents and references therein disclose various respiratory cartridges and protective equipment with ESLI for alerting when the cartridge or the protective equipment is exhausted, thereby requiring replacement: Yablick M.; (U.S. Pat. Nos. 1,537,519 and 1,725,893), Wing R. E.; (U.S. Pat. No. 4,365,627), McAllister J. W.; (U.S. Pat. No. 4,155,358), Leichnitz K.; (U.S. Pat. No. 4,684,380), Curado L.; (U.S. Pat. No. 6,497,756 B1), May W.; (U.S. Pat. No. 5,297,544), Bernard P.; (U.S. Pat. No. 6,375,725), Attar; (U.S. Pat. No. 7,503,962), Kirollos; (U.S. Pat. No. 7,927,558). In all the above mentioned devices, to apply an ESLI to a filter or a respiratory cartridge, major modifications should be done to the filter or the respiratory cartridge to accommodate the ESLI. In case of colorimetric ESLI, the filter or the respiratory cartridge housing should be at least partly clear to allow user to observe color change. The indicator should be placed inside the filter or respiratory cartridge in such manner that will not obstruct fluid flow through the filter or respiratory cartridge or causing channeling that deem the device ineffective. Further, filters and respiratory cartridges by themselves have no shelf-live. Inserting an ESLI into filters or respiratory cartridges during the manufacturing process require manufacturers to provide shelf-live date or use-before date, after which the device cannot be used. This limitation causes major logistic and inventory control burden for both manufacturers and end users.

BRIEF SUMMARY OF THE INVENTION

It is a general objective of the present invention to overcome the drawbacks of the prior art by providing a reliable and cost effective device or means to indicate the exhaustion and saturation of sorbent media.

A primary objective of the present invention is to provide a direct-read device capable of real-time visual indication of the exhaustion of sorbent media.

Another object of the present invention is to provide a device capable of the indication of the exhaustion of sorbent media without being affected by the surrounding environment.

Another objective of the present invention is to provide a device capable of real time, reliable indication of the exhaustion of sorbent media when operating at any humidity and light conditions.

A further objective of the present invention is to provide a universal device capable of being applied to any sorbent media device with minimum or no modification to the sorbent media device or the SMEI.

Another objective of the SMEI of the present invention is to ensure the safety of personnel using the sorbent media devices and to protect the environment from being polluted by toxic fluids emissions.

Yet another objective of the present invention is to provide low capacity and highly sensitive indicator capable of changing color upon exposure to toxic fluids at the part per million (ppm) and part per billion (ppb) levels.

It is a further objective of the present invention is to provide an indicator device that indicates the actual exhaustion and saturation and not the age of sorbent media.

Figure 1:
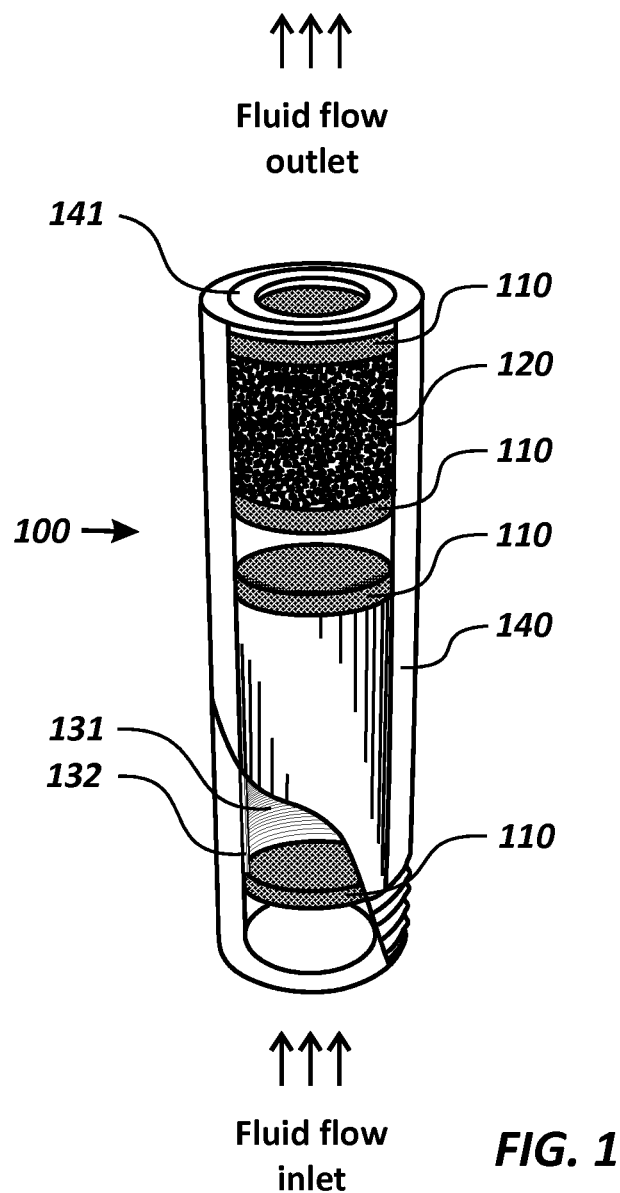
FIG. 1 is a schematic drawing of the present invention.

LIST OF NUMERALS 100 is the SMEI assembly
110 is porous plug
120 is trap member
130 is colorimetric sensor
131 is active ingredient(s) member of the colorimetric sensor
132 is colorimetric sensor support member
133 is an auxiliary support member
140 is housing member
141 is a porous plug guard member
150 is an auxiliary trap member
160 is a remote electronic alarm member
161 is an electronic alarm subsystem
162 is audio alarm
163 is image reader
164 is a transceiver A
165 is a transceiver B
166 is a wireless link
167 is base station
168 is power supply

DETAILED DESCRIPTION OF THE INVENTION

The present invention is a sorbent media exhaustion indicator (SMEI), generally indicated 100 in the figures, as will be described more fully herein below, when inserted into the outlet of a sorbent media device it will change color when the sorbent media is exhausted and saturated, hence alerting the user to replace the sorbent media device.

In operation, the SMEI fluid inlet is connected to the fluid outlet of the sorbent media device. The clean fluid flow from the outlet of the sorbent media device flows freely through the SMEI to the outside environment. Once the sorbent media is exhausted and saturated, and breakthrough of toxic contaminant fluids occurs, the contaminated fluids enter the SMEI and react with the colorimetric sensor producing visible color change that alerts the user of the exhaustion of the sorbent media.

In a preferred embodiment of the SMEI 100 of the present invention, the housing member 140 is a transparent plastic or glass, preferably having the shape of a hollow cylinder, but it can be a hollow polyhedron prism such as triangular prism, rectangular prism or pentagonal prism. The housing member 140 is preferably constructed from any clear durable plastic that incorporates light and thermal stabilizers such as polycarbonate, polyester, acrylic, polystyrene and the like.

In yet another preferred embodiment of the SMEI 100 of the present invention, the inside and or the outside walls of the housing member 140 are covered with a clear transparent thin layer of light and thermal stabilizers.

The porous plug 110 functions to localize the different components of the SMEI in place while allowing free fluid flow through the SMEI. The porous plug 110 has width and shape similar to the size and shape of the inside of the housing member 140. For example a cylindrical housing member 140 will have cylindrical plugs 110 and a triangular prism housing member 140 will have triangular prism plugs 110. The porous plug 110 is constructed from inert porous material; preferably plastic such as polypropylene, polyethylene and Teflon or porous porcelain or porous glass or porous metal.

In operation the colorimetric sensor 130 changes color upon exposure to trace amounts of toxic fluids. The colorimetric sensor 130 can be chemically designed to target a single toxic fluid such as ammonia or hydrogen sulfide or a group of toxic fluids such as acids and/or bases, ketones and/or alcohols.

The colorimetric sensor 130 comprises an inert transparent or opaque, fixable or rigid, porous or non-porous, flat or granular support member 132 and active ingredient(s) member 131. A flat support member 132 is preferably constructed from inert plastic such as polyester or polypropylene but it can be glass or cellulose. A granular support member 132 is preferably constructed from silica, glass or zeolite. An example of the active ingredient(s) member 131 that change color with acids is methyl orange or any acid/base indicator capable of changing color when pH drops below 7. Another example of the active ingredient(s) member 131 that changes from white to black in presence of hydrogen sulfide is lead acetate. One preferred embodiment of the colorimetric sensor 130 comprises the active ingredient(s) member 131 deposited or coated on one side of the support member 132.

Another preferred embodiment of the sensor 130 comprises the active ingredient(s) member 131, deposited or coated on both sides of support member 132. In yet another preferred embodiment of the colorimetric sensor 130, the active ingredient(s) member 131 is impregnated into a porous support member 132.

The trap member 120 functions to trap and prevent toxic fluid contaminants exist in the surrounding environment from entering the SMEI and changing the color of the colorimetric sensor 130, hence preventing false positive indication of the exhaustion of the sorbent media. Another function of the trap member 120 is to trap any toxic contaminants from exiting the SMEI when sorbent media breakthrough occurs and the colorimetric sensor 130 changes color, hence providing the user some time to stop operation and replace the sorbent media device and not being subjected to exposure to toxic fluids in the workplace environment. Yet another function of the trap member 120 is to absorb any humidity inside the SMEI during storage time, keeping the colorimetric sensor 130 in dry condition and absorb any humidity entering the SMEI from the surrounding environment, hence extending the shelf-life and service-life of the SMEI.

The trap member 120 comprises granular sorbent media preferably constructed from charcoal, impregnated charcoal and/or silica, impregnated silica and/or zeolite or any suitable sorbent media.

In an alternative embodiment, the trap member 120 can be one way valve, check valve or non-return valve that allow fluid flow to exit the SMEI and prevent fluids in the surrounding environment from entering the SMEI and hence producing false indication of the sorbent media exhaustion.

The auxiliary support member 133 functions to support and/or localize the colorimetric sensor(s) in place and/or regulate the fluids flow through the SMEI, and in front of the active ingredient(s) member 131. The auxiliary support member 133 is preferably constructed from inert non-porous or porous material preferably plastic such as polypropylene, polyethylene, Teflon or any suitable material capable of satisfying the intended function of the auxiliary support member 133.

Figure 4A:
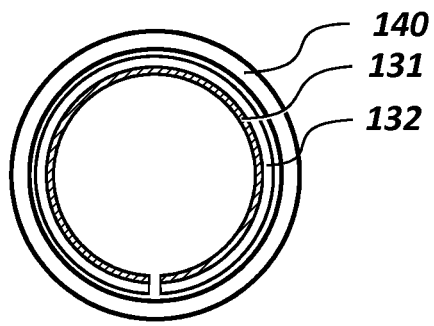
FIG. 4A is a cross-section view of the SMEI of the present invention depicted in FIG. 1.

Now referring to FIG. 1, in a preferred embodiment of the SMEI 100, the housing member 140 comprises a transparent hollow cylinder having a male threading at the inlet to allow convenient attachment to a female threaded outlet of the sorbent media device. The first two porous plugs 110 from the bottom functions to localize the colorimetric sensor 130 in place. In this preferred embodiment, the colorimetric sensor 130 comprises a transparent inert flexible support member 132 and active ingredient(s) member 131 coated or deposited on one side of the support member 132. The colorimetric sensor 130 is positioned above the threaded area of the housing member 140 having the active ingredient(s) member 131 facing the inside of the SMEI and the support member 132 facing the inside wall of the housing member 140, thus allowing the active ingredient(s) member 131 readily exposed to any traces of toxic fluids flowing through the SMEI when sorbent media breakthrough occurs, and at the same time allowing the user to observe any color change from all direction, FIG. 4A is a cross section view of FIG. 1. The trap member 120 is positioned on top of the SMEI near the outlet, and localized in place with two porous plugs 110. The porous plug guard 141 is positioned above the top plug 110, sealed to or screwed into the inside wall of the housing member 140. The porous plug guard 141 functions to secure the trap member 120 and top plug 110 in place in situations of wide diameter SMEI and/or high speed fluid flows.

Figure 2:
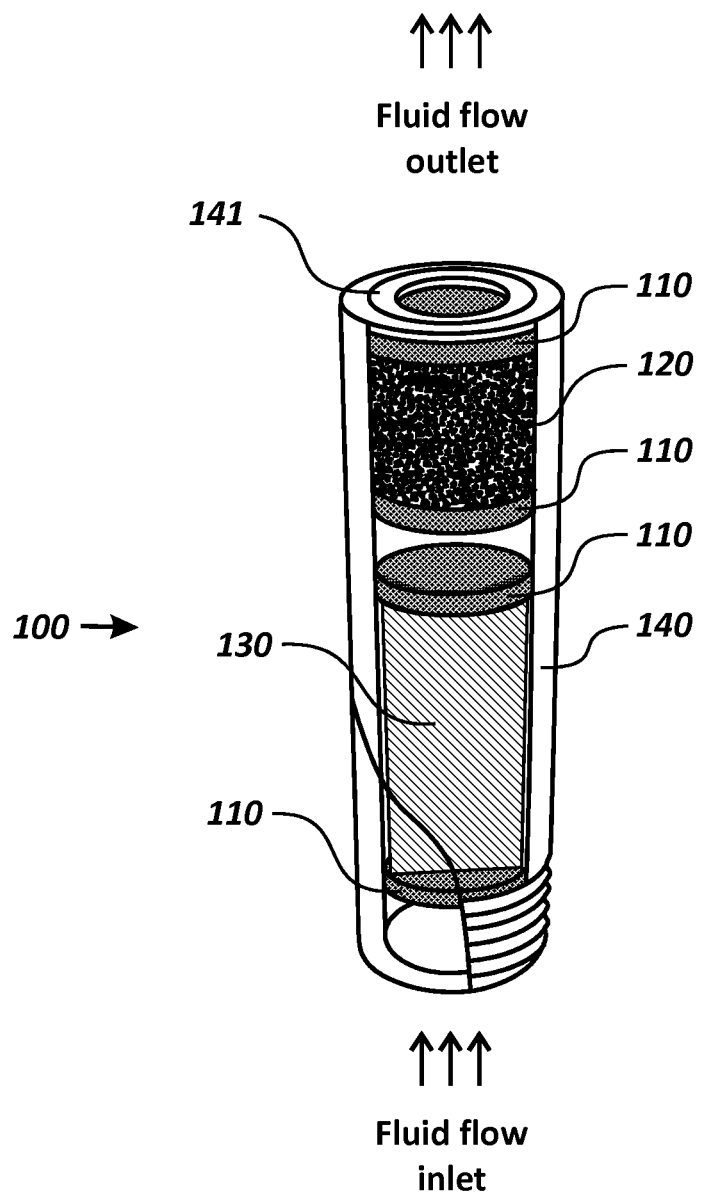
FIG. 2 is an alternative schematic drawing of the present invention.
Figure 4B:
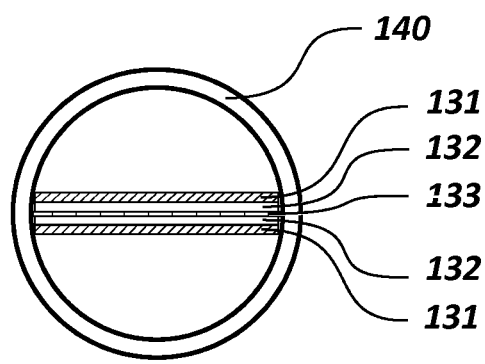
FIG. 4B is a cross-section view of the SMEI of the present invention depicted in FIG. 2.

Referring to FIG. 2 in a preferred embodiment of the SMEI 100, the colorimetric sensor 130 comprises active ingredient (s) member 131 coated or deposited on both sides of an inert flat flexible or rigid, transparent or opaque support member 132, the colorimetric sensor 130 having the shape of square or rectangle with a width equal to the inside diameter of the housing member 140 and positioned in the center, localized with two porous plugs 110, one above and one under the colorimetric sensor 130. In an alternative embodiment of 100 illustrated in FIG. 2, two colorimetric sensors 130 comprises active ingredient(s) member 131 coated or deposited on one side of a flat flexible or rigid, transparent or opaque support member 132. The two colorimetric sensors 130 are positioned at the center of the cylindrical housing 140 with the support members 132 facing each other, separated by an auxiliary support member 133; FIG. 4B is a cross section view of the alternative embodiment in FIG. 2.

Figure 3:
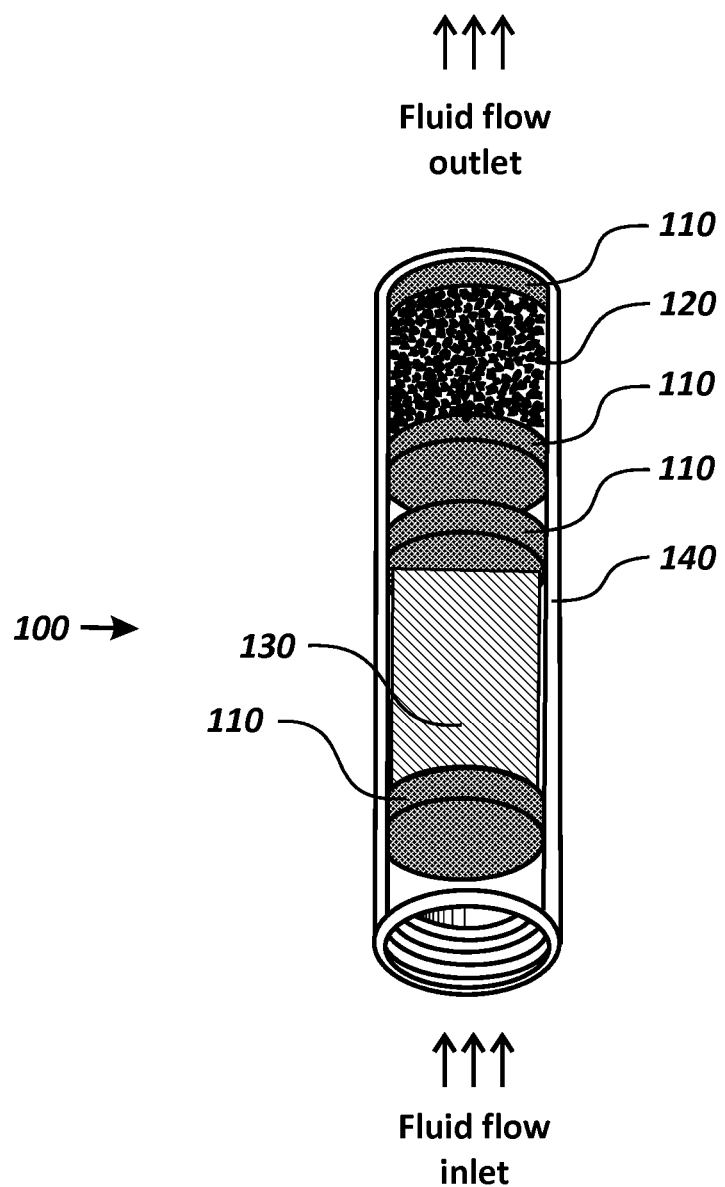
FIG. 3 is yet another alternative schematic drawing of the present invention.

FIG. 3 is another alternative preferred embodiment of the SMEI 100 illustrated in FIG. 1 and FIG. 2, wherein the housing member 140 comprises a transparent hollow cylinder having a female threading at the inlet to allow convenient attachment to a male threaded outlet of the sorbent media device.

Figure 4C:
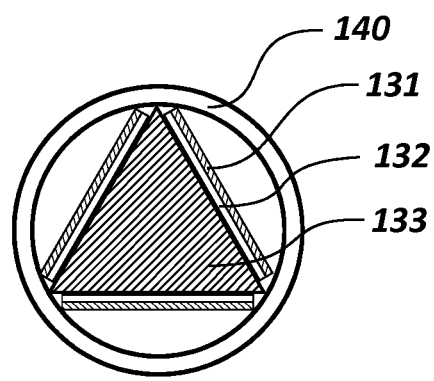
FIG. 4C is a cross-section view of the SMEI of the present invention wherein three colorimetric sensors positioned to form triangular prism.

FIG. 4C is an alternative cross section view of the SMEI 100, having three colorimetric sensors 130 positioned to form a triangular prism. In FIG. 4C the colorimetric sensors 130 comprises active ingredient(s) member 131 coated or deposited on one side of an inert flat flexible or rigid, transparent or opaque support member 132, having the active ingredient(s) members 131 facing out and exposed to the fluid flow, while the supports members 132 facing the auxiliary support member 133. The auxiliary support member 133 is having a shape of triangular prism to support the three colorimetric sensors 130 in place. The three colorimetric sensors 130 can be comprised of three identical colorimetric sensors targeting the same individual contaminant fluid or the same group of contaminant fluids or different individual contaminant fluids or different groups of contaminant fluids.

Figure 4D:
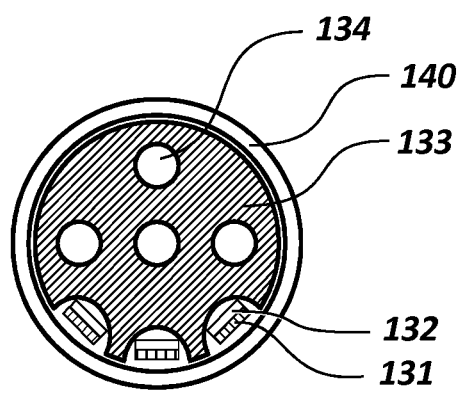
FIG. 4D is a cross-section view of the SMEI of the present invention wherein an auxiliary support member shaped in a manner to immobilize three colorimetric sensors in one side of the SMEI.

FIG. 4D, is yet another alternative variation of cross section view of the SMEI 100 having the auxiliary support member 133 shaped in a manner to immobilize three colorimetric sensors 130 in one side of the SMEI to allow the user to observe the results from one direction, comprising the auxiliary support member 133 having fluid flow openings 134 for optimizing fluid flow in front of the colorimetric sensors 130.

Figure 4E:
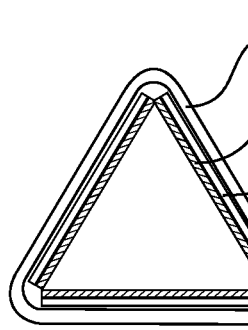
FIG. 4E is a cross-section view of the SMEI of the present invention wherein the housing member having the shape of triangular prism and comprising three colorimetric sensors.

FIG. 4E is cross sectional view of another preferred embodiment of the SMEI 100 wherein the housing member 140 has the shape of triangular prism, comprising three colorimetric sensors 130 wherein the support member 132 constructed from a flat transparent rigid or flexible plastic and the active ingredient(s) member 131 is coated or deposited on one side of the support member 132. In this embodiment, the colorimetric sensors 130 are positioned in such a manner wherein the active ingredient(s) members 131 are facing the inside of the SMEI and directly exposed to the fluid flow, whereas the transparent support members 132 facing the inside wall of the housing member 140. In this embodiment, when the sorbent media breakthrough occurs, the active ingredient(s) members 131 change color and the user observes the color change through the transparent housing member 140 and the transparent support member 132. The colorimetric sensors 130 in the preferred embodiment depicted in FIG. 4E can be designed to detect one fluid contaminant, a group of fluid contaminants, three different individual fluid contaminants or three different groups of fluid contaminants.

Figure 5:
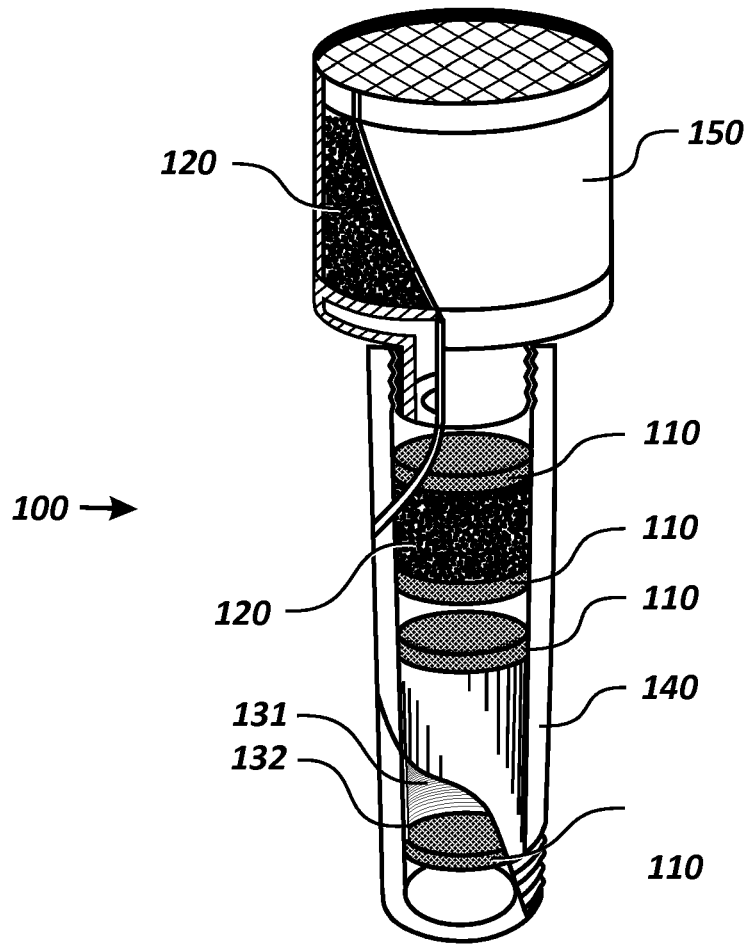
FIG. 5 is yet another alternative schematic drawing of the present invention wherein an auxiliary trap member is attached.

Referring to FIG. 5, in a preferred embodiment of the present invention, the SMEI 100 comprises a male threading at the bottom of the housing member 140 for convenient attachment to the outlet of the sorbent media devices and a female threading at the outlet wherein an auxiliary trap member 150 is connected. The auxiliary trap member 150 functions to increase the capacity of trapping contaminant fluids from entering the SMEI 100 from the surrounding environment through the fluid flow outlet. Yet another function of the auxiliary trap member 150 is to increase the capacity of trapping contaminant fluids from escaping to the outside environment when the sorbent media breakthrough occurs. The auxiliary trap member 150 comprises of a sorbent media device such as commercially available respiratory filter cartridges.

Figure 6:
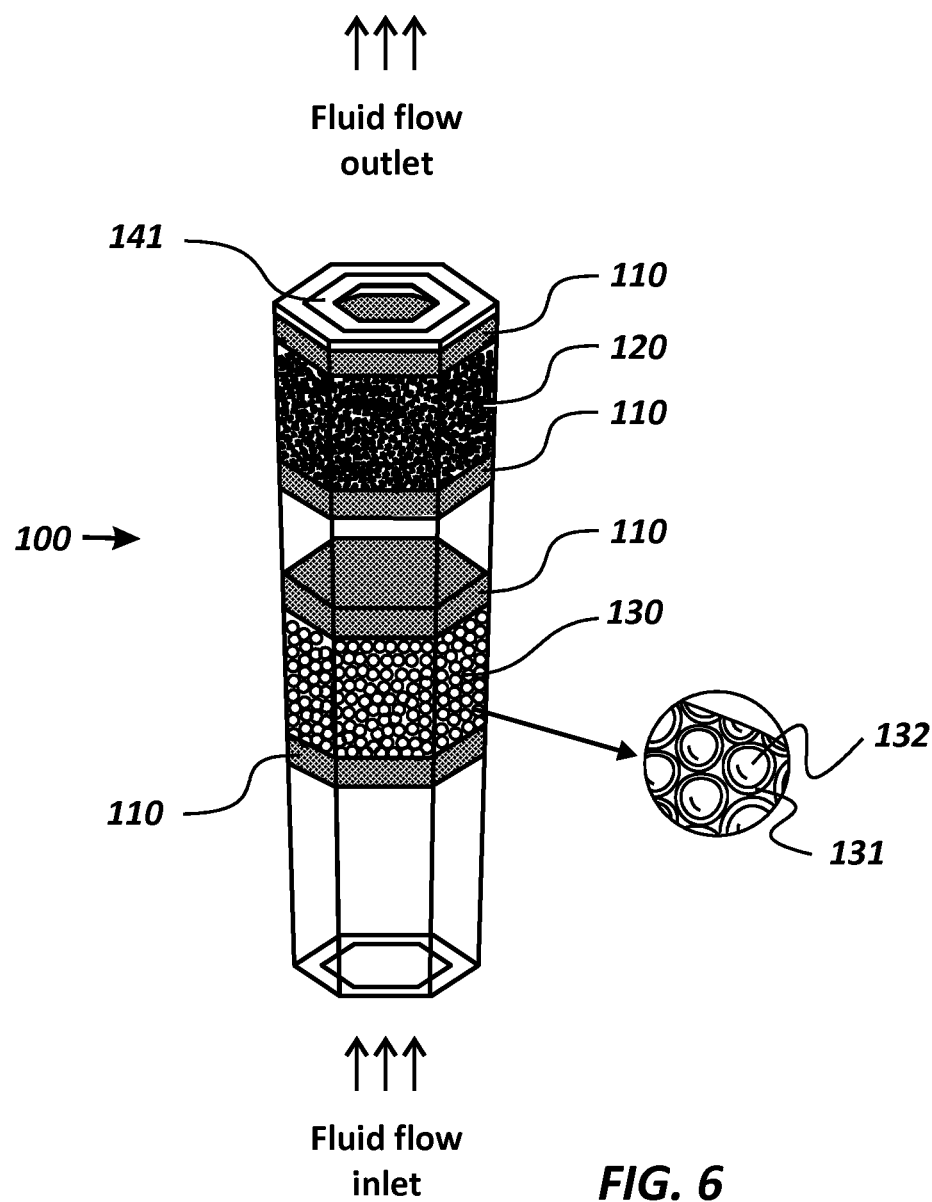
FIG. 6 is another alternative schematic drawing of the present invention wherein the housing member having the shape of hexagonal prism.

Referring to FIG. 6, in a yet another preferred embodiment of the present invention, the SMEI 100 comprises the housing member 140 having the shape of hexagonal prism, wherein, the colorimetric sensor 130 comprises of a granular nonporous support member 132 such as glass and the colorimetric ingredient(s) member 131 is coated or deposited on the surface of the support member 132. In an alternative composition of the colorimetric sensor 130 in this embodiment, the support member 132 comprises a granular porous substrate such as silica and the colorimetric ingredient(s) member 131 is impregnated in the support member 132.

Figure 7:
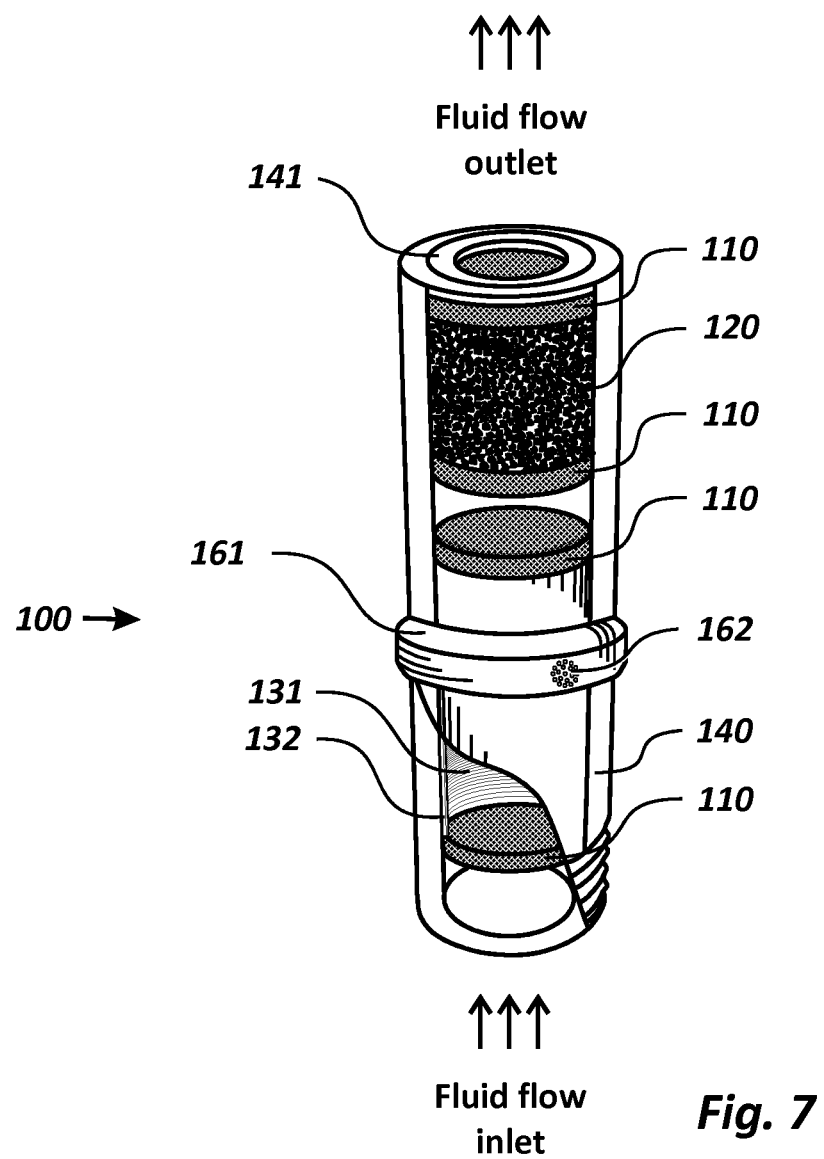
FIG. 7 is another preferred embodiment of the present invention wherein a remote electronic alarm member is incorporated.

Now referring to FIG. 7, in a preferred embodiment of the present invention, the SMEI 100 comprises a remote electronic alarm member 160. In operation, upon the exhaustion of the sorbent media device and the breakthrough of fluid contaminants occurs; the colorimetric sensor 130 changes color; the electronic alarm subsystem 161 takes an image of the colorimetric sensor 130 and sends a wireless message through the wireless link 166 to base station 167 and/or generates an audio alarm to warn the user of the exhaustion of the sorbent media device.

Figure 8:
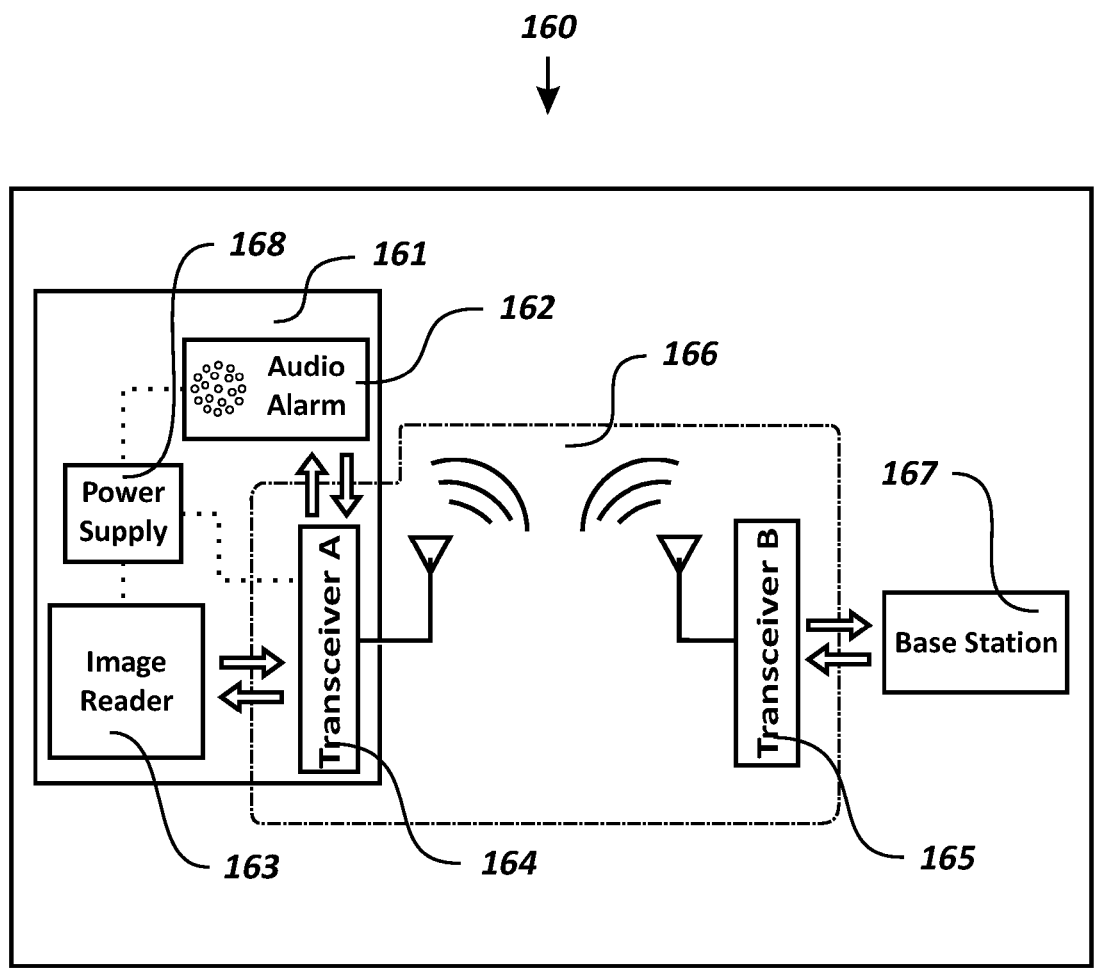
FIG. 8 is a schematic drawing of the remote electronic alarm member.

Referring to FIG. 8, the remote electronic alarm member 160 comprises three main components namely; an electronic alarm subsystem 161, a wireless link 166 and a base station 167. The electronic alarm subsystem 161 comprises an image reader 163, an audio alarm 162 and a power supply 168. The image reader 163 comprises an optical electronic sensor and other supporting devices and components such as microcontroller, lens and light source; this is where the image acquisition and analysis takes place. Based on this analysis, the electronic alarm subsystem 161 generates a text message that will be transmitted via wireless link 166 to base station 167. The wireless link 166 comprises of transceiver A 164 and transceiver B 165. The base station 167 comprises a computer, PC, laptop, smart phone, iPhone or any electronic device having the hardware and software that is capable of satisfying the intended functions of the base station described herein.

In one embodiment of the present invention, the image reader 163 uses an optical electronic sensor such as Complementary Metal Oxide Semiconductor (CMOS) sensor or Charge Coupled Device (CCD) sensor. The data from the image reader will be processed and a text message will be transmitted via the wireless link 166 such as Radio Frequency Identification (RFID) tag to a remote portable RFID reader. The data from the reader will be uploaded to base station 167 for assessment to determine whether corrective actions should be taken. In an alternative embodiment, other remote sensing capabilities such a low-power, active, RFID and a no-power, passive, RFID or other commercially available wireless technologies can also be used as an alternative to RFID.

The optical electronic sensor, such as the CMOS sensor, is programmed using a two-wire serial interface. This interface is between the optical electronic sensor and a microcontroller. This programming is necessary to access and make use of the control registers of the optical electronic sensor. These control registers dictate factors such as the rate at which the output data of the optical electronic sensor is read, the on chip analog-to-digital converter of the optical electronic sensor and other image processing components. An external Random Access Memory (RAM) chip is included to provide extra memory needed to hold the images produced by the optical electronic sensor.

A light source, such as a light emitting diode (LED), is integrated into the image reader 163 that provides adequate lighting during the time of image acquisition. This is accomplished by using one of the general purpose input/output (i/o) pins of the microcontroller. The microcontroller is programmed to generate an output voltage at one of the i/o pins just before the image is taken. This voltage serves as the power source for the LED.

In a preferred embodiment of the present invention, the output of the optical electronic sensor used is in the form of RGB (red, green, blue) values. Each pixel of the optical electronic sensor contains red, green and blue components that, when combined, produce the unique color that is captured from the colorimetric sensor 130. The RGB information obtained during image acquisition will then be given to the microcontroller where the image is processed and a decision of whether or not a color change has occurred will be made.

The data obtained from the optical electronic sensor are raw RGB data. This data is given to the microcontroller and analyzed. The particular color that will appear on the colorimetric sensor 130 after chemical exposure will be recorded and the corresponding RGB values will be used in an algorithm that will make the decision of whether or not a chemical exposure has been detected. The optical electronic sensor takes an initial reading of the colorimetric sensor 130 before any chemical exposure. The RGB values obtained from this reading will be treated as black, since the RGB values for black are all 0. This would be the equivalent of "zeroing" the optical electronic sensor. Any additional red or green or blue components will be analyzed to determine if a contaminant fluid has been detected. After the sensor has been zeroed, it will then be ready to take images of the colorimetric sensor 130 that will then be analyzed to decide whether a color change has occurred. An algorithm is implemented using embedded C code. The code is run on a dedicated microcontroller. At this stage, contaminant fluid has been detected. A text message containing this information will be generated and made ready for transmission. The algorithm will begin after the optical electronic sensor has taken an image of the unexposed colorimetric sensor 130. The RGB match decision will determine if the RGB values coming in from the optical electronic sensor match any of the values corresponding to the unique color produced by the colorimetric sensor 130. These recorded values will include the color of colorimetric sensor 130 before chemical exposure and the unique colors that the colorimetric sensor 130 will turn after chemical exposure.

The wireless link 166 is comprised of two commercially available transceivers 164 and 165 that serves as the wireless link stated above.

Once the message has been generated, it will be transmitted wirelessly to a remote lab or base station 167 where further action can be taken. This is accomplished by using two transceivers. One is interfaced to the optical electronic sensor subsystem, and the other is interfaced to the base station 167. The transceiver B 165 at the base station end is able to send a signal to the transceiver A 164 at the electronic alarm subsystem end and tell it to initiate the algorithm. Once the process described in the algorithm has been completed, the message generated will be sent to the transceiver B 165 at the base station 167 end.

In one embodiment of the present invention, the wireless link 166 is an RFID systems comprise of a reader/interrogator and a tag. The former is referred to as a reader when the tag is read only. It is referred to as an interrogator when the tag has both read and writes capabilities. In one embodiment of the present invention, the tag only requires read capabilities therefore; the term reader is used. It should be noted that although the tag will only require read capabilities from the reader, it will also be written to by the optical electronic sensor. The RFID tags can be either passive or active. The passive tag draws its power from the electromagnetic energy provided by the reader. In this way, the tag does not require a separate power supply, and as such, the remote monitoring system 161 would consume less power as a whole. Active tags are larger than passive tags and require a power supply. This difference in power requirements is partially due to the fact that active tags transmit a longer distance. The tag serves as the transceiver at the optical electronic sensor end, when not in use; the tag will be in sleep mode. The reader will then send a signal to the tag to wake it and tell it to send an interrupt signal to the image reader 163. This triggers the image reader to take an image of the colorimetric sensor 130. From there, the process will be as described above, where the image is taken, processed and a text message is generated.

In yet another embodiment of the present invention the wireless link 166 is a radio module such as the Laird Tech. radio module which employs a 900 MHz FHSS technology. This wireless link offers a peer-to-peer protocol and a 20 mile transmission range.

Several embodiments of the present invention have been described herein. It should be understood by those of ordinary skill in the art, however, that the above described embodiments, are set forth merely by way of example and should not be interpreted as limiting the scope of the invention. Other alternative embodiments, variations and modifications of the foregoing embodiments that embrace various aspects of the present invention will also be understood upon a reading of the detailed description in light of the prior art.

What we claim:

1. A sorbent media exhaustion indicator for indicating the saturation and exhaustion of sorbent media devices by forming a visual color change, said sorbent media exhaustion indicator comprising:
   a transparent housing member (140) having the shape of a hollow cylinder or a hollow polyhedron prism, the housing member comprising
   at least two porous plugs (110), one above the other, which function to localize the different components of the sorbent media exhaustion indicator while allowing free flow of fluids through the sorbent media exhaustion indicator, wherein the indicator comprises at least one colorimetric sensor (130) between the porous plugs that changes color upon exposure to toxic fluids, said colorimetric sensor having one support member and at least one active ingredient member;
   at least one trap member (120) which functions to prevent fluids from entering the sorbent media exhaustion indicator from surrounding environment;
   at least one auxiliary support member (133) which functions to support and localize the colorimetric sensor in place and regulate fluids flow of fluids through the sorbent media exhaustion indicator;
   at least one porous plug guard member (141) positioned above the top porous plug (110), sealed to or screwed into the inside wall of the housing member (140);
   an auxiliary trap member (150) which functions to increase the capacity of trapping contaminant fluids from escaping to the surrounding environment when sorbent media breakthrough occurs and functions to trap contaminant fluids in the surrounding environment and prevent them from entering the sorbent media exhaustion indicator; and
   a remote electronic alarm member (160) that sends a wireless message and generates an audio alarm to alert the user when the sorbent media exhaustion indicator changes color, said remote electronic alarm member (160) comprises an electronic alarm subsystem (161), a wireless link (166) and base station (167).

2. The sorbent media exhaustion indicator of claim 1 wherein said a housing member is transparent plastic or transparent glass.

3. The sorbent media exhaustion indicator of claim 1 wherein said a housing member further comprises at least one female or male threading for convenient attachment to sorbent media devices and to auxiliary trap member.

4. The sorbent media exhaustion indicator of claim 1 wherein said a housing member further comprises a thin transparent layer of light and thermal stabilizers coated on the inside wall or the outside wall.

5. The sorbent media exhaustion indicator of claim 1 wherein said porous plug is having the shape and size of the inside cross section of said housing member.

6. The sorbent media exhaustion indicator of claim 1 wherein said support member is a clear or opaque inert material.

7. The sorbent media exhaustion indicator of claim 1 wherein said support member is flexible or rigid inert material.

8. The sorbent media exhaustion indicator of claim 1 wherein said support member is a flat or granular inert material.

9. The sorbent media exhaustion indicator of claim 1 wherein said active ingredient member is coated on at least one side of the said support member.

10. The sorbent media exhaustion indicator of claim 1 wherein said active ingredient member is impregnated on at least one side of the said support member.

11. The sorbent media exhaustion indicator of claim 1 wherein said trap member comprises granular sorbent media capable of adsorbing and trapping toxic fluids.

12. The sorbent media exhaustion indicator of claim 1 wherein said trap member comprises one-way valve capable of allowing fluids to exit the sorbent media exhaustion indicator and prevent fluids in the surrounding environment from entering the sorbent media exhaustion indicator.

13. The sorbent media exhaustion indicator of claim 1 wherein said auxiliary support member comprises inert porous or none porous material.

14. The sorbent media exhaustion indicator of claim 1 wherein said auxiliary trap member is a sorbent media device.

15. The sorbent media exhaustion indicator of claim 1 wherein said electronic alarm subsystem comprises an image reader (163), audio alarm (162) and power supply (168).

16. The sorbent media exhaustion indicator of claim 1 wherein said base station comprises a computer, laptop or smart phone.

\* \* \* \* \*